(12) United States Patent
Locke et al.

(10) Patent No.: US 11,179,275 B2
(45) Date of Patent: Nov. 23, 2021

(54) METHODS FOR MANUFACTURING AND ASSEMBLING DUAL MATERIAL TISSUE INTERFACE FOR NEGATIVE-PRESSURE THERAPY

(71) Applicant: KCI Licensing, Inc., San Antonio, TX (US)

(72) Inventors: Christopher Brian Locke, Bournemouth (GB); John Elwood, Clarinbridge (IE)

(73) Assignee: KCI Licensing, Inc., San Antonio, TX (US)

( * ) Notice: Subject to any disclaimer, the term of this patent is extended or adjusted under 35 U.S.C. 154(b) by 0 days.

(21) Appl. No.: 16/876,299

(22) Filed: May 18, 2020

(65) Prior Publication Data

US 2020/0276058 A1 Sep. 3, 2020

Related U.S. Application Data

(63) Continuation of application No. 15/997,931, filed on Jun. 5, 2018, now Pat. No. 10,695,227.
(Continued)

(51) Int. Cl.
*A61F 13/00* (2006.01)
*A61F 13/02* (2006.01)
(Continued)

(52) U.S. Cl.
CPC .. *A61F 13/00995* (2013.01); *A61F 13/00068* (2013.01); *A61F 13/00987* (2013.01);
(Continued)

(58) Field of Classification Search
CPC ............ A61F 13/00995; A61F 13/0216; A61F 13/00987; A61F 13/00068; B32B 27/065;
(Continued)

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Daniel McNally

(57) ABSTRACT

A dressing for treating tissue with negative pressure may be a composite of dressing layers, including a release film, perforated gel layer, a perforated polymer film, a manifold, and an adhesive cover. A method of manufacturing the dressing may comprise providing a first layer, such as the gel layer, on a substrate, perforating the first layer on the substrate to create a plurality of apertures in the first layer, and creating an index of the plurality of apertures in the first layer. A laser can be calibrated based on the index. A second layer, such as the polymer film, may be coupled to the first layer, and a plurality of slots can be cut in the second layer with the laser. Each of the slots can be cut through one of the apertures in the first layer based on the index.

6 Claims, 7 Drawing Sheets

Related U.S. Application Data

(60) Provisional application No. 62/623,325, filed on Jan. 29, 2018, provisional application No. 62/616,244, filed on Jan. 11, 2018, provisional application No. 62/615,821, filed on Jan. 10, 2018, provisional application No. 62/613,494, filed on Jan. 4, 2018, provisional application No. 62/592,950, filed on Nov. 30, 2017, provisional application No. 62/576,498, filed on Oct. 24, 2017, provisional application No. 62/565,754, filed on Sep. 29, 2017, provisional application No. 62/516,540, filed on Jun. 7, 2017, provisional application No. 62/516,550, filed on Jun. 7, 2017, provisional application No. 62/516,566, filed on Jun. 7, 2017.

(51) Int. Cl.
| | | |
|---|---|---|
| *B23K 26/00* | (2014.01) | |
| *B23K 26/38* | (2014.01) | |
| *B32B 5/18* | (2006.01) | |
| *B32B 7/06* | (2019.01) | |
| *B32B 7/12* | (2006.01) | |
| *B32B 27/06* | (2006.01) | |
| *B32B 27/30* | (2006.01) | |
| *B32B 27/32* | (2006.01) | |
| *B32B 37/12* | (2006.01) | |
| *B32B 37/18* | (2006.01) | |
| *A61M 1/00* | (2006.01) | |

(52) U.S. Cl.
CPC ...... *A61F 13/0216* (2013.01); *B23K 26/0006* (2013.01); *B23K 26/38* (2013.01); *B32B 5/18* (2013.01); *B32B 7/06* (2013.01); *B32B 7/12* (2013.01); *B32B 27/065* (2013.01); *B32B 27/308* (2013.01); *B32B 27/32* (2013.01); *B32B 37/12* (2013.01); *B32B 37/182* (2013.01); *A61M 1/90* (2021.05); *B32B 2255/10* (2013.01); *B32B 2255/20* (2013.01); *B32B 2255/205* (2013.01); *B32B 2255/24* (2013.01); *B32B 2255/26* (2013.01); *B32B 2266/0221* (2013.01); *B32B 2266/0278* (2013.01); *B32B 2266/06* (2013.01); *B32B 2266/124* (2016.11); *B32B 2305/022* (2013.01); *B32B 2307/724* (2013.01); *B32B 2307/728* (2013.01); *B32B 2307/7265* (2013.01); *B32B 2307/73* (2013.01); *B32B 2310/0843* (2013.01); *B32B 2323/04* (2013.01); *B32B 2329/04* (2013.01); *B32B 2331/04* (2013.01); *B32B 2333/08* (2013.01); *B32B 2375/00* (2013.01); *B32B 2535/00* (2013.01)

(58) Field of Classification Search
CPC ......... B32B 27/32; B32B 27/308; B32B 7/12; B32B 7/06; B32B 37/182; B32B 37/12; B32K 26/18; B32K 26/38; B32K 26/0006
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,654,060 A | 4/1972 | Goldman |
| 3,682,180 A | 8/1972 | McFarlane |
| 3,826,254 A | 7/1974 | Mellor |
| 3,930,096 A | 12/1975 | Gilpatrick |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,173,046 A | 11/1979 | Gallagher |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,541,426 A | 9/1985 | Webster |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,308,313 A | 5/1994 | Karami et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |

(56) References Cited

U.S. PATENT DOCUMENTS

| | | |
|---|---|---|
| 5,449,352 A | 9/1995 | Nishino et al. |
| 5,466,231 A | 11/1995 | Cercone et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,635,201 A | 6/1997 | Fabo |
| 5,636,643 A | 6/1997 | Argenta et al. |
| 5,645,081 A | 7/1997 | Argenta et al. |
| 5,720,714 A | 2/1998 | Penrose |
| 5,842,503 A | 12/1998 | Foley |
| 5,951,505 A | 9/1999 | Gilman et al. |
| 5,981,822 A | 11/1999 | Addison |
| 6,019,511 A | 2/2000 | Thomas et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,468,626 B1 | 10/2002 | Takai et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,653,523 B1 | 11/2003 | McCormack et al. |
| 6,685,681 B2 | 2/2004 | Lockwood et al. |
| 6,752,794 B2 | 6/2004 | Lockwood et al. |
| 6,814,079 B2 | 11/2004 | Heaton et al. |
| 6,855,135 B2 | 2/2005 | Lockwood et al. |
| 7,195,624 B2 | 3/2007 | Lockwood et al. |
| 7,338,482 B2 | 3/2008 | Lockwood et al. |
| 7,381,859 B2 | 6/2008 | Hunt et al. |
| 7,534,927 B2 | 5/2009 | Lockwood et al. |
| 7,846,141 B2 | 12/2010 | Weston |
| 7,867,206 B2 | 1/2011 | Lockwood et al. |
| 7,880,050 B2 | 2/2011 | Robinson et al. |
| 7,896,864 B2 | 3/2011 | Lockwood et al. |
| 7,951,100 B2 | 5/2011 | Hunt et al. |
| 7,988,680 B2 | 8/2011 | Lockwood et al. |
| 8,062,273 B2 | 11/2011 | Weston |
| 8,148,595 B2 | 4/2012 | Robinson et al. |
| 8,168,848 B2 | 5/2012 | Lockwood et al. |
| 8,187,210 B2 | 5/2012 | Hunt et al. |
| 8,216,198 B2 | 7/2012 | Heagle et al. |
| 8,246,592 B2 | 8/2012 | Lockwood et al. |
| 8,251,979 B2 | 8/2012 | Malhi |
| 8,257,327 B2 | 9/2012 | Blott et al. |
| 8,350,116 B2 | 1/2013 | Lockwood et al. |
| 8,398,614 B2 | 3/2013 | Blott et al. |
| 8,449,509 B2 | 5/2013 | Weston |
| 8,454,580 B2 | 6/2013 | Locke et al. |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,672,903 B2 | 3/2014 | Hunt et al. |
| 8,679,081 B2 | 3/2014 | Heagle et al. |
| 8,680,359 B2 | 3/2014 | Robinson et al. |
| 8,690,844 B2 | 4/2014 | Locke et al. |
| 8,834,451 B2 | 9/2014 | Blott et al. |
| 8,884,094 B2 | 11/2014 | Lockwood et al. |
| 8,926,592 B2 | 1/2015 | Blott et al. |
| 9,017,302 B2 | 4/2015 | Vitaris et al. |
| 9,168,179 B2 | 10/2015 | Robinson et al. |
| 9,198,801 B2 | 12/2015 | Weston |
| 9,198,802 B2 | 12/2015 | Robinson et al. |
| 9,211,365 B2 | 12/2015 | Weston |
| 9,289,542 B2 | 3/2016 | Blott et al. |
| 9,352,075 B2 | 5/2016 | Robinson et al. |
| 9,445,947 B2 | 9/2016 | Hunt et al. |
| 9,526,660 B2 | 12/2016 | Robinson et al. |
| 9,844,471 B2 | 12/2017 | Lockwood et al. |
| 10,016,544 B2 | 7/2018 | Coulthard et al. |
| 10,045,886 B2 | 8/2018 | Lockwood et al. |
| 2001/0043943 A1 | 11/2001 | Coffey |
| 2002/0077661 A1 | 6/2002 | Saadat |
| 2002/0082567 A1 | 6/2002 | Lockwood et al. |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0203011 A1 | 10/2003 | Abuelyaman et al. |
| 2004/0030304 A1 | 2/2004 | Hunt et al. |
| 2004/0126413 A1 | 7/2004 | Sigurjonsson et al. |
| 2004/0138604 A1 | 7/2004 | Sigurjonsson et al. |
| 2004/0148756 A1 | 8/2004 | Pommer |
| 2004/0261295 A1 | 12/2004 | Meschter |
| 2006/0241542 A1 | 10/2006 | Gudnason et al. |
| 2007/0038172 A1 | 2/2007 | Zamierowski |
| 2007/0185426 A1 | 8/2007 | Ambrosio et al. |
| 2008/0300555 A1 | 12/2008 | Olson et al. |
| 2009/0047495 A1 | 2/2009 | Hubbs |
| 2009/0082746 A1 | 3/2009 | Thomas et al. |
| 2009/0221979 A1 | 9/2009 | Huang et al. |
| 2009/0234307 A1 | 9/2009 | Vitaris |
| 2009/0293887 A1 | 12/2009 | Wilkes et al. |
| 2010/0030178 A1 | 2/2010 | MacMeccan et al. |
| 2010/0036334 A1 | 2/2010 | Heagle et al. |
| 2010/0063484 A1 | 3/2010 | Heagle |
| 2010/0069863 A1 | 3/2010 | Olson |
| 2010/0106115 A1 | 4/2010 | Hardman et al. |
| 2010/0159192 A1 | 6/2010 | Cotton |
| 2010/0291184 A1 | 11/2010 | Clark et al. |
| 2010/0305490 A1 | 12/2010 | Coulthard et al. |
| 2011/0054422 A1 | 3/2011 | Locke et al. |
| 2011/0117178 A1 | 5/2011 | Junginger |
| 2011/0160686 A1 | 6/2011 | Ueda et al. |
| 2011/0213287 A1 | 9/2011 | Lattimore et al. |
| 2011/0224631 A1 | 9/2011 | Simmons et al. |
| 2011/0282309 A1 | 11/2011 | Adie et al. |
| 2011/0313374 A1 | 12/2011 | Lockwood et al. |
| 2012/0046603 A1 | 2/2012 | Vinton |
| 2012/0157945 A1 | 6/2012 | Robinson et al. |
| 2012/0209226 A1 | 8/2012 | Simmons et al. |
| 2012/0238932 A1 | 9/2012 | Atteia et al. |
| 2013/0053748 A1 | 2/2013 | Cotton |
| 2013/0152945 A1 | 6/2013 | Locke et al. |
| 2013/0261534 A1 | 10/2013 | Niezgoda et al. |
| 2014/0031771 A1 | 1/2014 | Locke et al. |
| 2014/0052041 A1 | 2/2014 | Barberio |
| 2014/0094730 A1 | 4/2014 | Greener et al. |
| 2014/0107562 A1 | 4/2014 | Dorian et al. |
| 2014/0163447 A1 | 6/2014 | Wieland et al. |
| 2014/0163491 A1 | 6/2014 | Schuessler et al. |
| 2014/0188059 A1 | 7/2014 | Robinson et al. |
| 2014/0200532 A1 | 7/2014 | Robinson et al. |
| 2014/0228787 A1 | 8/2014 | Croizat et al. |
| 2014/0236112 A1 | 8/2014 | Von Wolff et al. |
| 2014/0350494 A1 | 11/2014 | Hartwell et al. |
| 2014/0364819 A1 | 12/2014 | VanDelden |
| 2015/0038933 A1 | 2/2015 | Day et al. |
| 2015/0057624 A1 | 2/2015 | Simmons et al. |
| 2015/0080788 A1 | 3/2015 | Blott et al. |
| 2015/0119830 A1 | 4/2015 | Luckemeyer et al. |
| 2015/0119831 A1 | 4/2015 | Robinson et al. |
| 2015/0141941 A1 | 5/2015 | Allen et al. |
| 2015/0174291 A1 | 6/2015 | Zimnitsky et al. |
| 2015/0174304 A1 | 6/2015 | Askem et al. |
| 2015/0290042 A1 | 10/2015 | Freer et al. |
| 2015/0290050 A1 | 10/2015 | Wada |
| 2015/0320434 A1 | 11/2015 | Ingram et al. |
| 2015/0320602 A1 | 11/2015 | Locke et al. |
| 2015/0320603 A1 | 11/2015 | Locke et al. |
| 2016/0000610 A1 | 1/2016 | Riesinger |
| 2016/0015571 A1 | 1/2016 | Robinson et al. |
| 2016/0022885 A1 | 1/2016 | Dunn et al. |
| 2016/0030646 A1 | 2/2016 | Hartwell et al. |
| 2016/0144084 A1 | 5/2016 | Collinson et al. |
| 2016/0144085 A1 | 5/2016 | Melin et al. |
| 2016/0166744 A1 | 6/2016 | Hartwell |
| 2016/0199546 A1 | 7/2016 | Chao |
| 2016/0199550 A1 | 7/2016 | Seddon et al. |
| 2016/0220742 A1 | 8/2016 | Robinson et al. |
| 2016/0262672 A1 | 9/2016 | Hammond et al. |
| 2016/0354253 A1 | 12/2016 | Hunt et al. |
| 2017/0014273 A1 | 1/2017 | Woodroof |

(56) References Cited

U.S. PATENT DOCUMENTS

| | | | |
|---|---|---|---|
| 2017/0079846 | A1 | 3/2017 | Locke et al. |
| 2017/0095374 | A1 | 4/2017 | Lauer |
| 2017/0143552 | A1* | 5/2017 | Hartwell ............ A61F 13/0233 |
| 2017/0172807 | A1 | 6/2017 | Robinson et al. |
| 2017/0209312 | A1 | 7/2017 | Kanchagar et al. |
| 2017/0258640 | A1 | 9/2017 | Ahsani Ghahreman et al. |
| 2017/0312406 | A1 | 11/2017 | Svensby |
| 2017/0348154 | A1 | 12/2017 | Robinson et al. |
| 2018/0071148 | A1 | 3/2018 | Lockwood et al. |
| 2018/0289872 | A1 | 10/2018 | Coulthard et al. |
| 2018/0296394 | A1 | 10/2018 | Barberio |
| 2019/0184075 | A1 | 6/2019 | Roos |

FOREIGN PATENT DOCUMENTS

| | | |
|---|---|---|
| AU | 755496 B2 | 12/2002 |
| CA | 2005436 A1 | 6/1990 |
| CN | 106390213 A | 2/2017 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0174803 A2 | 3/1986 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| GB | 2468905 A | 9/2010 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 9319709 A1 | 10/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2001/085248 A1 | 11/2001 |
| WO | 2007113597 A2 | 10/2007 |
| WO | 2010061228 A1 | 6/2010 |
| WO | 2011/008497 A2 | 1/2011 |
| WO | 201121127 A1 | 10/2011 |
| WO | 2011135286 A1 | 11/2011 |
| WO | 2014140608 A1 | 9/2014 |
| WO | 2015098373 A1 | 7/2015 |
| WO | 2015/173547 A1 | 11/2015 |
| WO | 2015168681 A1 | 11/2015 |
| WO | 2015193257 A1 | 12/2015 |
| WO | 2016014645 A1 | 1/2016 |
| WO | 2016015001 A2 | 1/2016 |
| WO | 2017040045 A1 | 3/2017 |
| WO | 2017119996 A1 | 7/2017 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 pages English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 pages English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

(56) References Cited

OTHER PUBLICATIONS

G. Živadinovi?, V. ?uki?, Ž. Maksimovi?, ?. Radak, and P. Peška, "Vacuum Therapy in the Treatment of Peripheral Bood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax, " Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
3M™ Medical Tape 9830, Single Sided Transparent Polyethylene, 63# Liner, Configurable. Retrieved on May 21, 2019. Retrieved from the Internet: <www.3m.com/3M/en_US/company-us/all-3m-products/~/3M-9830-Transparent-Polyethylene-Single-Sided-Medical-Tape-63-Liner/?N=5002385+8729793+3294739632&rt=rud; accessed May 21, 2019>.
3M™ Medical Tape 9948, Single Sided Thermoplastic Elastomer Medical Tape, 63# liner, Configurable. Retrieved May 21, 2019. Retrieved from the Internet: <www.3m.com/3M/en_US/company-us/all-3m-products/~/3M-9948-Single-Bided-Thermoplastic-Elastomer-TPE-Medical-Incise-Tape/?N=5002385+4294834151&rt=d; accessed May 21, 2019>.
International Search Report and Written Opinion for related application PCT/US2018/036013, dated Aug. 7, 2018.
International Search Report and Written Opinion for related application PCT/US2018/035945, dated Aug. 24, 2018.
International Search Report and Written Opinion for related application PCT/US2018/036074, dated Aug. 24, 2018.
International Search Report and Written Opinion for related application PCT/US2018/035957, dated Sep. 28, 2018.
International Search Report and Written Opinion for related application PCT/US2018/035995, dated Oct. 1, 2018.
International Search Report and Written Opinion for related application PCT/US2018/036021, dated Aug. 24, 2018.
International Search Report and Written Opinion for related application PCT/US2018/036019, dated Oct. 18, 2018.
International Search Report and Written Opinion for related application PCT/US2018/036054, dated Aug. 24, 2018.
International Search Report and Written Opinion for related application PCT/US2018/036049, dated Aug. 29, 2018.
International Search Report and Written Opinion for related application PCT/US2018/036077, dated Aug. 24, 2018.
International Search Report and Written Opinion for related application PCT/US2018/036129, dated Oct. 8, 2018.
Heft, et al., "Foam Pore Size Is a Critical Interface Parameter of Suction-Based Wound Healing Devices," copyright 2012 by the American Society of Plastic Surgeons (www. PRSJournal.com) (Year: 2011).
Office Action for related U.S. Appl. No 16/000,284, dated Sep. 23, 2019.
Office Action for related U.S. Appl. No 16/000,284, dated Jun. 8, 2020.
Office Action for related U.S. Appl. No 15/997,833, dated Jun. 19, 2020.
Office Action for related U.S. Appl. No. 15/997,809, dated Aug. 5, 2020.
Law, Definitions for Hydrophilicity, Hydrophobicity, and Superhydrophobicity: Getting the Basics Right, The Journal of Physical Chemistry Letters, Feb. 20, 2014, 686-688.
Office Action for related U.S. Appl. No. 15/997,841, dated Aug. 5, 2020.
Office Action for related U.S. Appl. No. 15/997,818, dated Sep. 3, 2020.
Office Action for related U.S. Appl. No. 15/997,761, dated Sep. 14, 2020.
Office Action for related U.S. Appl. No. 15/997,923, dated Sep. 17, 2020.
Office Action for related U.S. Appl. No. 16/000,737, dated Sep. 29, 2020.
Office Action for related U.S. Appl. No. 16/000,002, dated Oct. 28, 2020.
Singaporean Office Action for related application 11201909383P, dated Oct. 5, 2020.
Singaporean Office Action for related application 11201909371P, dated Oct. 13, 2020.
Definition of "bonded," Merriam-Webster, www.https://www.merriam-webster.com/dictionary/bonded, retrieved Dec. 11, 2020.
Burkitt et al., "New Technologies in Silicone Adhesives: Silicone-based film adhesives, PSAs and tacky gels each offer unique advantages"; ASI (Adhesives & Sealants Industry), Aug. 1, 2012; https://www.adhesivesmag.com/articles/91217-new-technologies-in-silicone-adhesives.
Office Action for related U.S. Appl. No. 16/000,284, dated Nov. 25, 2020.
Office Action for related U.S. Appl. No. 16/000,411, dated Dec. 7, 2020.
Office Action for related U.S. Appl. No. 16/000,383, dated Jul. 8, 2020.
Bastarrachea et al. Engineering Properties of Polymeric-Based Antimicrobial Films for Food Packaging: A Review. Food Engineering Reviews. 3. 2011. pp. 79-93.
Selke et al. Packaging: Polymers for Containers, Encyclopedia of Materials: Science and Technology, Elsevier, 2001 pp. 6646-6652.
Office Action for related U.S. Appl. No. 16/000,368, dated Dec. 14, 2020.
Office Action for related U.S. Appl. No. 15/997,818, dated Jan. 27, 2021.
Office Action for related U.S. Appl. No. 15/997,841, dated Jan. 27, 2021.
Office Action for related U.S. Appl. No. 15/997,809, dated Jan. 28, 2021.
Office Action for related U.S. Appl. No. 15/997,833, dated Mar. 26, 2021.
Office Action for related U.S. Appl. No. 16/000,215, dated Apr. 12, 2021.
Chinese Office Action for related application 2018800367248, dated Apr. 28, 2021.
Office Action for related U.S. Appl. No. 15/997,833, dated Jun. 7, 2021.
Office Action for related U.S. Appl. No. 15/997,841, dated Jun. 8, 2021.

(56) References Cited

OTHER PUBLICATIONS

Chinese Office Action for related application 201880048393X, dated May 26, 2021.
Office Action for related U.S. Appl. No. 15/997,809, dated Jul. 8, 2021.
Chinese Office Action for related application 2018800436430, dated Jun. 8, 2021.
Office Action for related U.S. Appl. No. 15/997,923, dated Jul. 23, 2021.
Office Action for related U.S. Appl. No. 15/997,818, dated Aug. 10, 2021.
Office Action for related U.S. Appl. No. 16/684,060, dated Aug. 27, 2021.
Office Action for related U.S. Appl. No. 16/000,411, dated Aug. 27, 2021.
Office action for related U.S. Appl. No. 15/997,833, dated Sep. 7, 2021.

* cited by examiner

METHODS FOR MANUFACTURING AND ASSEMBLING DUAL MATERIAL TISSUE INTERFACE FOR NEGATIVE-PRESSURE THERAPY

RELATED APPLICATION

This application is a continuation of U.S. patent application Ser. No. 15/997,931, entitled "Methods for Manufacturing and Assembling Dual Material Tissue Interface for Negative-Pressure Therapy," filed Jun. 5, 2018, which claims the benefit, under 35 U.S.C. § 119(e), of the filing of U.S. Provisional Patent Application No. 62/623,325, entitled "Methods For Manufacturing And Assembling Dual Material Tissue Interface For Negative-Pressure Therapy," filed Jan. 29, 2018; U.S. Provisional Patent Application No. 62/616,244, entitled "Composite Dressings For Improved Granulation And Reduced Maceration With Negative-Pressure Treatment," filed Jan. 11, 2018; U.S. Provisional Patent Application No. 62/615,821, entitled "Methods For Manufacturing And Assembling Dual Material Tissue Interface For Negative-Pressure Therapy," filed Jan. 10, 2018; U.S. Provisional Patent Application No. 62/613,494, entitled "Peel And Place Dressing For Thick Exudate And Instillation," filed Jan. 4, 2018; U.S. Provisional Patent Application No. 62/592,950, entitled "Multi-Layer Wound Filler For Extended Wear Time," filed Nov. 30, 2017; U.S. Provisional Patent Application No. 62/576,498, entitled "Systems, Apparatuses, And Methods For Negative-Pressure Treatment With Reduced Tissue In-Growth," filed Oct. 24, 2017; U.S. Provisional Patent Application No. 62/565,754, entitled "Composite Dressings For Improved Granulation And Reduced Maceration With Negative-Pressure Treatment," filed Sep. 29, 2017; U.S. Provisional Patent Application No. 62/516,540, entitled "Tissue Contact Interface," filed Jun. 7, 2017; U.S. Provisional Patent Application No. 62/516,550, entitled "Composite Dressings For Improved Granulation And Reduced Maceration With Negative-Pressure Treatment" filed Jun. 7, 2017; and U.S. Provisional Patent Application No. 62/516,566, entitled "Composite Dressings For Improved Granulation And Reduced Maceration With Negative-Pressure Treatment" filed Jun. 7, 2017, each of which are incorporated herein by reference for all purposes.

TECHNICAL FIELD

The invention set forth in the appended claims relates generally to tissue treatment systems and more particularly, but without limitation, to methods of manufacturing a dual material tissue interface for negative-pressure therapy.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound or a cavity can be washed out with a stream of liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and/or instillation therapy are widely known, improvements to therapy systems, components, and processes may benefit healthcare providers and patients.

BRIEF SUMMARY

New and useful systems, apparatuses, and methods for treating tissue in a negative-pressure therapy environment are set forth in the appended claims. Illustrative embodiments are also provided to enable a person skilled in the art to make and use the claimed subject matter.

For example, in some embodiments, a dressing for treating tissue may be a composite of dressing layers including a release film, perforated gel layer, a perforated polymer film, a manifold, and an adhesive cover. The manifold may be reticulated foam in some examples, and may be relatively thin and hydrophobic to reduce the fluid hold capacity of the dressing. The manifold may also be thin to reduce the dressing profile and increase flexibility, which can enable it to conform to wound beds and other tissue sites under negative pressure. In some embodiments, the perforations may be slits or slots.

The perforation pattern of the polymer film can be aligned with the perforation pattern of at least a central area of the gel layer. For example, in some embodiments, the gel layer may be perforated and indexed on a liner, and the polymer film can loaded and fixed to the gel layer. The combined laminate can be presented to a laser. The position of a laser mask can be calibrated to an underside of the dressing, referencing perforations in the gel layer to calibrate its position. The laser can then be fired, creating centrally registered slots in the polymer film within the perforations of the gel layer.

More generally, a method of manufacturing a dressing for negative-pressure treatment may comprise providing a first layer, such as the gel layer, on a substrate, perforating the first layer on the substrate to create a plurality of apertures in the first layer, and creating an index of the plurality of apertures in the first layer. A laser can be calibrated based on the index. A second layer, such as the polymer film, may be coupled to the first layer, and a plurality of slots can be cut in the second layer with the laser. Each of the slots can be cut through one of the apertures in the first layer based on the index.

Objectives, advantages, and a preferred mode of making and using the claimed subject matter may be understood best

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
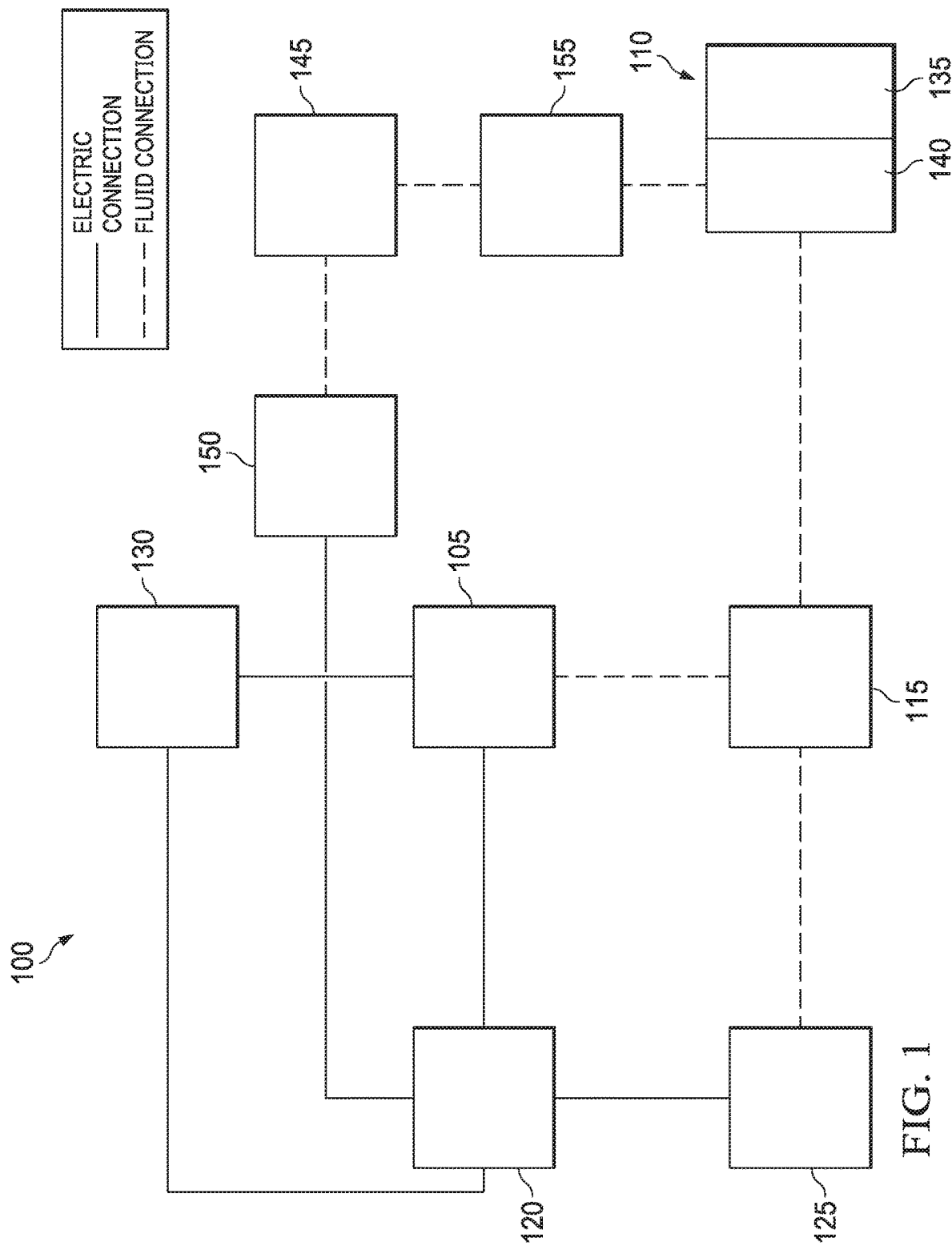
FIG. 1 is a functional block diagram of an example embodiment of a therapy system that can provide negative-pressure treatment and instillation treatment in accordance with this specification.

FIG. 1 is a simplified functional block diagram of an example embodiment of a therapy system 100 that can provide negative-pressure therapy with instillation of topical treatment solutions to a tissue site in accordance with this specification.

The term "tissue site" in this context broadly refers to a wound, defect, or other treatment target located on or within tissue, including, but not limited to, a surface wound, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. A surface wound, as used herein, is a wound on the surface of a body that is exposed to the outer surface of the body, such as an injury or damage to the epidermis, dermis, and/or subcutaneous layers. Surface wounds may include ulcers or closed incisions, for example. A surface wound, as used herein, does not include wounds within an intra-abdominal cavity. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 105, a dressing 110, a fluid container, such as a container 115, and a regulator or controller, such as a controller 120, for example. Additionally, the therapy system 100 may include sensors to measure operating parameters and provide feedback signals to the controller 120 indicative of the operating parameters. As illustrated in FIG. 1, for example, the therapy system 100 may include a first sensor 125 and a second sensor 130 coupled to the controller 120. As illustrated in the example of FIG. 1, the dressing 110 may comprise or consist essentially of a tissue interface 135, a cover 140, or both in some embodiments.

The therapy system 100 may also include a source of instillation solution. For example, a solution source 145 may be fluidly coupled to the dressing 110, as illustrated in the example embodiment of FIG. 1. The solution source 145 may be fluidly coupled to a positive-pressure source such as the positive-pressure source 150, a negative-pressure source such as the negative-pressure source 105, or both in some embodiments. A regulator, such as an instillation regulator 155, may also be fluidly coupled to the solution source 145 and the dressing 110 to ensure proper dosage of instillation solution (e.g. saline) to a tissue site. For example, the instillation regulator 155 may comprise a piston that can be pneumatically actuated by the negative-pressure source 105 to draw instillation solution from the solution source during a negative-pressure interval and to instill the solution to a dressing during a venting interval. Additionally or alternatively, the controller 120 may be coupled to the negative-pressure source 105, the positive-pressure source 150, or both, to control dosage of instillation solution to a tissue site. In some embodiments, the instillation regulator 155 may also be fluidly coupled to the negative-pressure source 105 through the dressing 110, as illustrated in the example of FIG. 1.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 105 may be combined with the solution source 145, the controller 120, and other components into a therapy unit.

In general, components of the therapy system 100 may be coupled directly or indirectly. For example, the negative-pressure source 105 may be directly coupled to the container 115 and may be indirectly coupled to the dressing 110 through the container 115. Coupling may include fluid, mechanical, thermal, electrical, or chemical coupling (such as a chemical bond), or some combination of coupling in some contexts. For example, the negative-pressure source 105 may be electrically coupled to the controller 120 fluidly coupled to one or more distribution components to provide a fluid path to a tissue site. In some embodiments, components may also be coupled by virtue of physical proximity, being integral to a single structure, or being formed from the same piece of material.

A distribution component is preferably detachable and may be disposable, reusable, or recyclable. The dressing 110 and the container 115 are illustrative of distribution components. A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 110. For example, such a dressing interface may be a SENSA-T.R.A.C.™ Pad available from Kinetic Concepts, Inc. of San Antonio, Tex.

A negative-pressure supply, such as the negative-pressure source 105, may be a reservoir of air at a negative pressure or may be a manual or electrically-powered device. Examples of a suitable negative-pressure supply may include a vacuum pump, a suction pump, a wall suction port available at many healthcare facilities, or a micro-pump. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 115 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 120, may be a microprocessor or computer programmed to operate one or more components of the therapy system 100, such as the negative-pressure source 105. In some embodiments, for example, the controller 120 may be a microcontroller, which generally comprises an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the tissue interface 135, for example. The controller 120 is also preferably configured to receive one or more input signals, such as a feedback signal, and programmed to modify one or more operating parameters based on the input signals.

Sensors, such as the first sensor 125 and the second sensor, 130 are generally known in the art as any apparatus operable to detect or measure a physical phenomenon or property, and generally provide a signal indicative of the phenomenon or property that is detected or measured. For example, the first sensor 125 and the second sensor 130 may be configured to measure one or more operating parameters of the therapy system 100. In some embodiments, the first sensor 125 may be a transducer configured to measure pressure in a pneumatic pathway and convert the measurement to a signal indicative of the pressure measured. In some embodiments, for example, the first sensor 125 may be a piezo-resistive strain gauge. The second sensor 130 may optionally measure operating parameters of the negative-pressure source 105, such as a voltage or current, in some embodiments. Preferably, the signals from the first sensor 125 and the second sensor 130 are suitable as an input signal to the controller 120, but some signal conditioning may be appropriate in some embodiments. For example, the signal may need to be filtered or amplified before it can be processed by the controller 120. Typically, the signal is an electrical signal, but may be represented in other forms, such as an optical signal.

The tissue interface 135 can be generally adapted to partially or fully contact a tissue site. The tissue interface 135 may take many forms and may have many sizes, shapes, or thicknesses, depending on a variety of factors, such as the type of treatment being implemented or the nature and size of a tissue site. For example, the size and shape of the tissue interface 135 may be adapted to the contours of deep and irregular shaped tissue sites. Moreover, any or all of the surfaces of the tissue interface 135 may have projections or an uneven, coarse, or jagged profile that can induce strains and stresses on a tissue site, which can promote granulation at the tissue site.

In some embodiments, the tissue interface 135 may comprise or consist essentially of a manifold. A "manifold" in this context generally includes any substance or structure providing a plurality of pathways adapted to collect or distribute fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid, such as fluid from a source of instillation solution, across a tissue site.

In some illustrative embodiments, the pathways of a manifold may be interconnected to improve distribution or collection of fluids across a tissue site. In some illustrative embodiments, a manifold may be a porous foam material having interconnected cells or pores. For example, open-cell foam, porous tissue collections, and other porous material such as gauze or felted mat generally include pores, edges, and/or walls adapted to form interconnected fluid channels. Liquids, gels, and other foams may also include, or be cured to include, apertures and fluid pathways. In some embodiments, a manifold may additionally or alternatively comprise projections that form interconnected fluid pathways. For example, a manifold may be molded to provide surface projections that define interconnected fluid pathways.

The average pore size of foam may vary according to needs of a prescribed therapy. For example, in some embodiments, the tissue interface 135 may comprise or consist essentially of foam having pore sizes in a range of 400-600 microns. The tensile strength of the tissue interface 135 may also vary according to needs of a prescribed therapy. For example, the tensile strength of foam may be increased for instillation of topical treatment solutions. In some examples, the tissue interface 135 may be reticulated polyurethane foam such as found in GRANUFOAM™ dressing or V.A.C. VERAFLO™ dressing, both available from Kinetic Concepts, Inc. of San Antonio, Tex.

The tissue interface 135 may further promote granulation at a tissue site when pressure within the sealed therapeutic environment is reduced. For example, any or all of the surfaces of the tissue interface 135 may have an uneven, coarse, or jagged profile that can induce microstrains and stresses at a tissue site if negative pressure is applied through the tissue interface 135.

In some embodiments, the tissue interface 135 may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The tissue interface 135 may further serve as a scaffold for new cell-growth, or a scaffold material may be used in conjunction with the tissue interface 135 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 140 may provide a bacterial barrier and protection from physical trauma. The cover 140 may also be constructed from a material that can reduce evaporative losses and provide a fluid seal between two components or two environments, such as between a therapeutic environment and a local external environment. The cover 140 may comprise or consist of, for example, an elastomeric film or membrane that can provide a seal adequate to maintain a negative pressure at a tissue site for a given negative-pressure source. The cover 140 may have a high moisture-vapor transmission rate (MVTR) in some applications. For example, the MVTR may be at least 450 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties.

In some example embodiments, the cover 140 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. For example, the cover 140 may comprise one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polymide copolymers. Such materials are commercially available as, for example, Tegaderm® drape, commercially available from 3M Company, Minneapolis Minn.; polyurethane (PU) drape, commercially available from Avery Dennison Corporation, Pasadena, Calif.; polyether block polyamide copolymer (PEBAX), for example, from Arkema S.A., Colombes, France; and Inspire 2301 and Inpsire 2327 polyurethane films, commercially available from Expopack Advanced Coatings, Wrexham, United Kingdom. In some embodiments, the cover 140 may comprise INSPIRE 2301 having an MVTR (upright cup technique) of 2600 g/m$^2$/24 hours and a thickness of about 30 microns.

An attachment device may be used to attach the cover 140 to an attachment surface, such as undamaged epidermis, a gasket, or another cover. The attachment device may take many forms. For example, an attachment device may be a medically-acceptable, pressure-sensitive adhesive configured to bond the cover 140 to epidermis around a tissue site. In some embodiments, for example, some or all of the cover 140 may be coated with an adhesive, such as an acrylic adhesive, which may have a coating weight of 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The solution source 145 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

Figure 2:
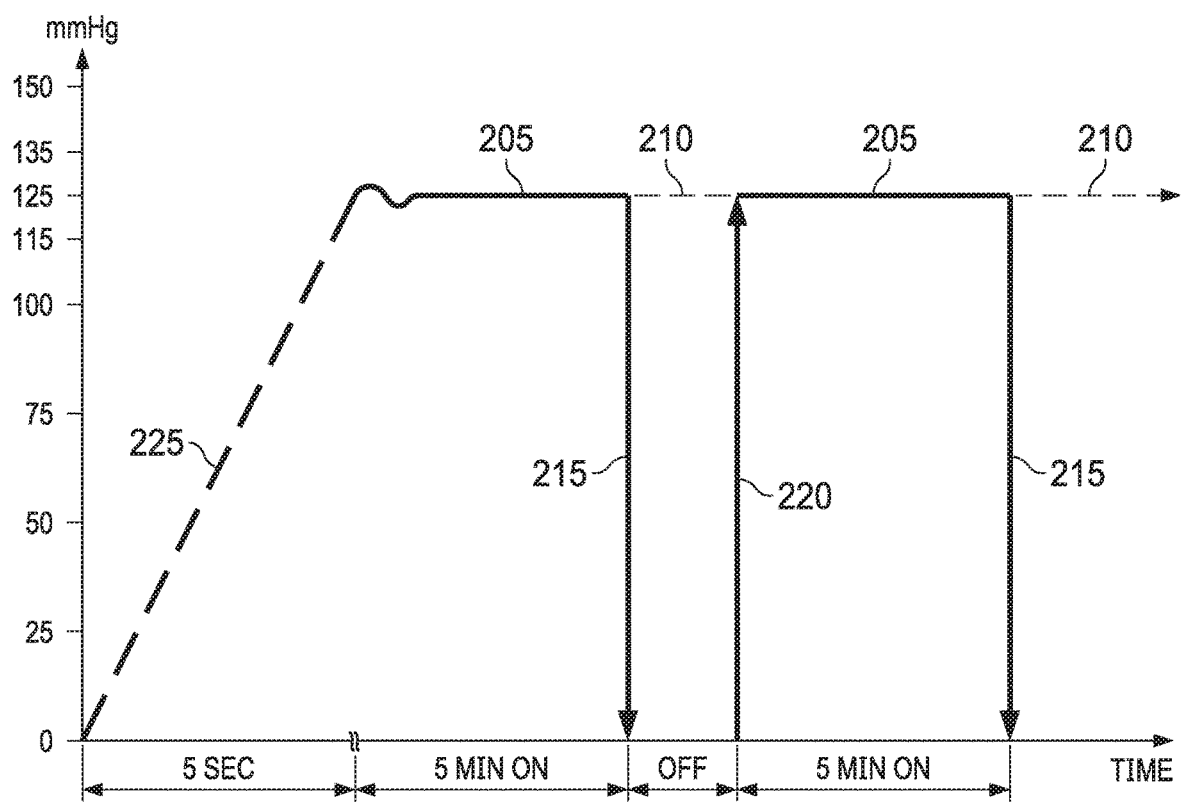
FIG. 2 is a graph illustrating additional details of example pressure control modes that may be associated with some embodiments of the therapy system of FIG. 1.

FIG. 2 is a graph illustrating additional details of an example control mode that may be associated with some embodiments of the controller 120. In some embodiments, the controller 120 may have a continuous pressure mode, in which the negative-pressure source 105 is operated to provide a constant target negative pressure, as indicated by line 205 and line 210, for the duration of treatment or until manually deactivated. Additionally or alternatively, the controller may have an intermittent pressure mode, as illustrated in the example of FIG. 2. In FIG. 2, the x-axis represents time, and the y-axis represents negative pressure generated by the negative-pressure source 105 over time. In the example of FIG. 2, the controller 120 can operate the negative-pressure source 105 to cycle between a target pressure and atmospheric pressure. For example, the target pressure may be set at a value of 125 mmHg, as indicated by line 205, for a specified period of time (e.g., 5 min), followed by a specified period of time (e.g., 2 min) of deactivation, as indicated by the gap between the solid lines 215 and 220. The cycle can be repeated by activating the negative-pressure source 105, as indicated by line 220, which can form a square wave pattern between the target pressure and atmospheric pressure.

In some example embodiments, the increase in negative-pressure from ambient pressure to the target pressure may not be instantaneous. For example, the negative-pressure source 105 and the dressing 110 may have an initial rise time, as indicated by the dashed line 225. The initial rise time may vary depending on the type of dressing and therapy equipment being used. For example, the initial rise time for one therapy system may be in a range of about 20-30 mmHg/second and in a range of about 5-10 mmHg/second for another therapy system. If the therapy system 100 is operating in an intermittent mode, the repeating rise time, as indicated by the solid line 220, may be a value substantially equal to the initial rise time as indicated by the dashed line 225.

Figure 3:
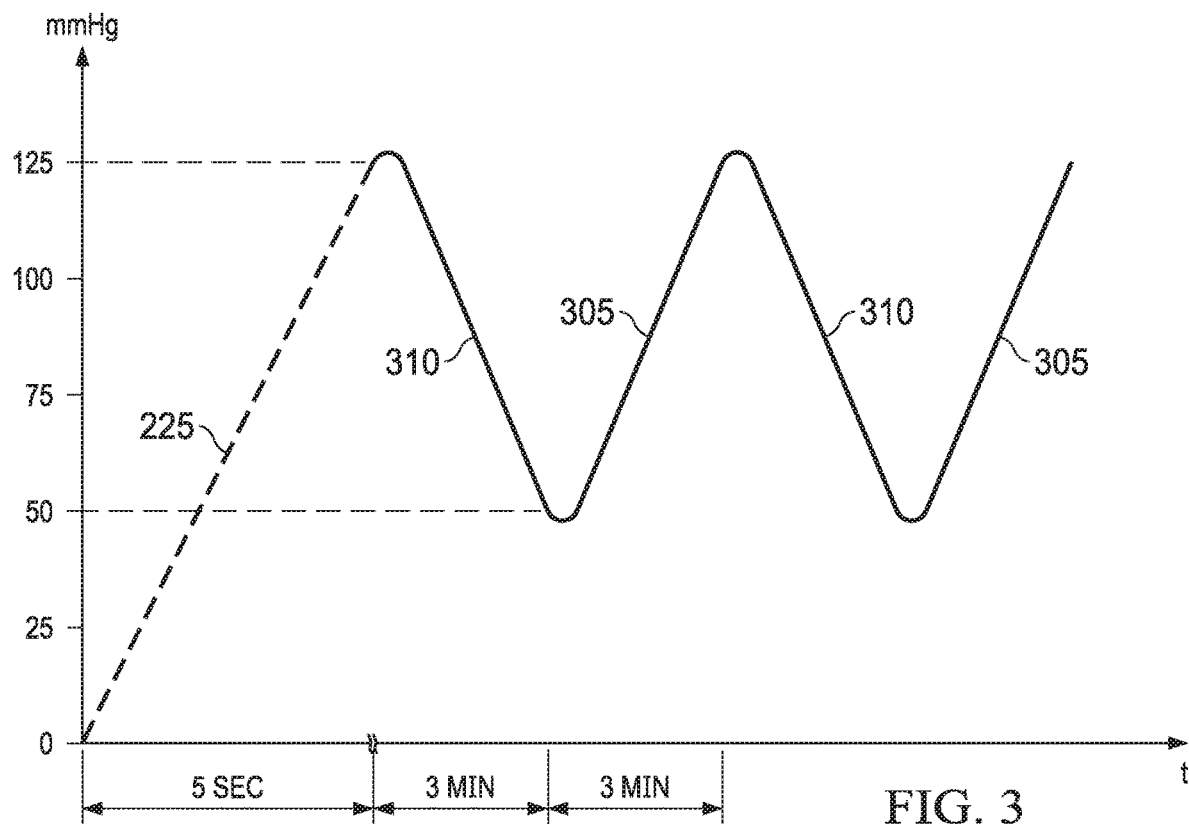
FIG. 3 is a graph illustrating additional details that may be associated with another example pressure control mode in some embodiments of the therapy system of FIG. 1.

FIG. 3 is a graph illustrating additional details that may be associated with another example pressure control mode in some embodiments of the therapy system 100. In FIG. 3, the x-axis represents time and the y-axis represents negative pressure generated by the negative-pressure source 105. The target pressure in the example of FIG. 3 can vary with time in a dynamic pressure mode. For example, the target pressure may vary in the form of a triangular waveform, varying between a negative pressure of 50 and 125 mmHg with a rise time 305 set at a rate of +25 mmHg/min. and a descent time 310 set at −25 mmHg/min. In other embodiments of the therapy system 100, the triangular waveform may vary between negative pressure of 25 and 125 mmHg with a rise time 305 set at a rate of +30 mmHg/min and a descent time 310 set at −30 mmHg/min.

In some embodiments, the controller 120 may control or determine a variable target pressure in a dynamic pressure mode, and the variable target pressure may vary between a maximum and minimum pressure value that may be set as an input prescribed by an operator as the range of desired negative pressure. The variable target pressure may also be processed and controlled by the controller 120, which can vary the target pressure according to a predetermined waveform, such as a triangular waveform, a sine waveform, or a saw-tooth waveform. In some embodiments, the waveform may be set by an operator as the predetermined or time-varying negative pressure desired for therapy.

Figure 4:
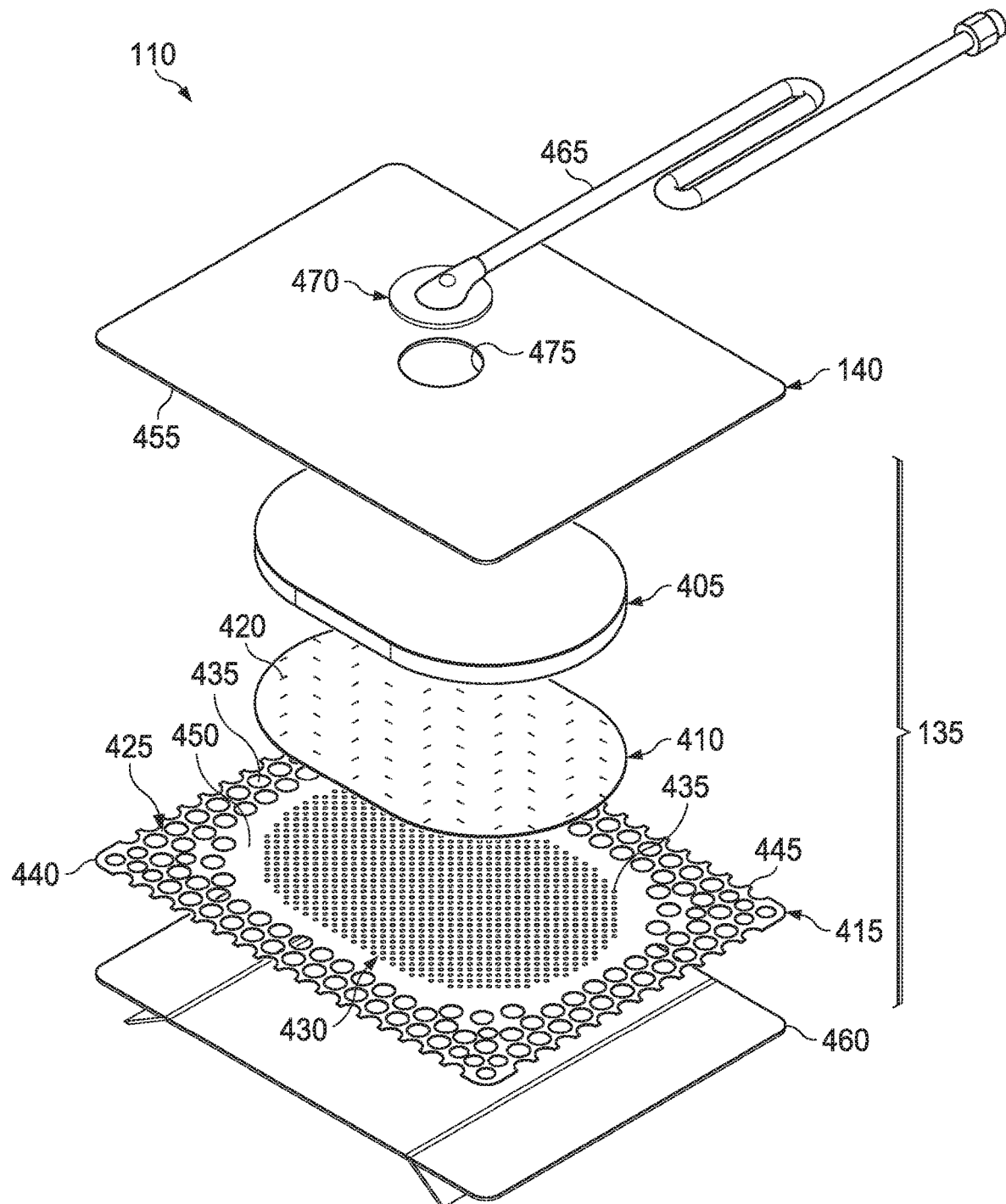
FIG. 4 is an assembly view of an example of a dressing that may be associated with some embodiments of the therapy system of FIG. 1.

FIG. 4 is an assembly view of an example of the dressing 110 of FIG. 1, illustrating additional details that may be associated with some embodiments in which the tissue interface 135 comprises more than one layer. In the example of FIG. 2, the tissue interface 135 comprises a manifold 405, a polymer film 410, and a gel layer 415. In some embodiments, the manifold 405 may be disposed adjacent to the polymer film 410, and the gel layer 415 may be disposed adjacent to the polymer film 410 opposite the manifold 405. For example, the manifold 405, the polymer film 410, and the gel layer 415 may be stacked so that the manifold 405 is in contact with the polymer film 410, and the polymer film 410 is in contact with the manifold 405 and the gel layer 415. One or more of the manifold 405, the polymer film 410, and the gel layer 415 may also be bonded to an adjacent layer in some embodiments.

The manifold 405 may comprise or consist essentially of a means for collecting or distributing fluid across the tissue interface 135 under pressure. For example, the manifold 405 may be adapted to receive negative pressure from a source and distribute negative pressure through multiple apertures across the tissue interface 135, which may have the effect of collecting fluid from across a tissue site and drawing the fluid toward the source. In some embodiments, the fluid path may be reversed or a secondary fluid path may be provided to facilitate delivering fluid, such as from a source of instillation solution, across the tissue interface 135.

In some illustrative embodiments, the manifold 405 may comprise a plurality of pathways, which can be interconnected to improve distribution or collection of fluids. In some embodiments, the manifold 405 may comprise or consist essentially of a porous material having interconnected fluid pathways. For example, open-cell foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, the manifold 405 may additionally or alternatively comprise projections that form interconnected fluid pathways. For example, the manifold 405 may be molded to provide surface projections that define interconnected fluid pathways. Any or all of the surfaces of the manifold 405 may have an uneven, coarse, or jagged profile.

In some embodiments, the manifold 405 may comprise or consist essentially of reticulated foam having pore sizes and free volume that may vary according to needs of a prescribed therapy. For example, reticulated foam having a free volume of at least 90% may be suitable for many therapy applications, and foam having an average pore size in a range of 400-600 microns (40-50 pores per inch) may be particularly suitable for some types of therapy. The tensile strength of the manifold 405 may also vary according to needs of a prescribed therapy. For example, the tensile strength of the manifold 405 may be increased for instillation of topical treatment solutions. The 25% compression load deflection of the manifold 405 may be at least 0.35 pounds per square inch, and the 65% compression load deflection may be at least 0.43 pounds per square inch. In some embodiments, the tensile strength of the manifold 405 may be at least 10 pounds per square inch. The manifold 405 may have a tear strength of at least 2.5 pounds per inch. In some embodiments, the manifold 405 may be foam comprised of polyols such as polyester or polyether, isocyanate such as toluene diisocyanate, and polymerization modifiers such as amines and tin compounds. In one non-limiting example, the manifold 405 may be a reticulated polyurethane ether foam such as used in GRANUFOAM™ dressing or V.A.C. VERAFLO™ dressing, both available from KCI of San Antonio, Tex.

The thickness of the manifold 405 may also vary according to needs of a prescribed therapy. For example, the thickness of the manifold 405 may be decreased to relieve stress on other layers and to reduce tension on peripheral tissue. The thickness of the manifold 405 can also affect the conformability of the manifold 405. In some embodiments, a thickness in a range of about 5 millimeters to 10 millimeters may be suitable.

The polymer film 410 may comprise or consist essentially of a means for controlling or managing fluid flow. In some embodiments, the polymer film 410 may comprise or consist essentially of a liquid-impermeable, elastomeric polymer. The polymer film 410 may also have a smooth or matte surface texture in some embodiments. A glossy or shiny finish better or equal to a grade B3 according to the SPI (Society of the Plastics Industry) standards may be particularly advantageous for some applications. In some embodiments, variations in surface height may be limited to acceptable tolerances. For example, the surface of the polymer film 410 may have a substantially flat surface, with height variations limited to 0.2 millimeters over a centimeter.

In some embodiments, the polymer film 410 may be hydrophobic. The hydrophobicity of the polymer film 410 may vary, and may have a contact angle with water of at least ninety degrees in some embodiments. In some embodiments the polymer film 410 may have a contact angle with water of no more than 150 degrees. For example, in some embodiments, the contact angle of the polymer film 410 may be in a range of at least 90 degrees to about 120 degrees or in a range of at least 120 degrees to 150 degrees. Water contact angles can be measured using any standard apparatus. Although manual goniometers can be used to visually approximate contact angles, contact angle measuring instruments can often include an integrated system involving a level stage, liquid dropper such as a syringe, camera, and software designed to calculate contact angles more accurately and precisely, among other things. Non-limiting examples of such integrated systems may include the FTÅ125, FTÅ200, FTÅ2000, and FTÅ4000 systems, all commercially available from First Ten Angstroms, Inc., of Portsmouth, Va., and the DTA25, DTA30, and DTA100 systems, all commercially available from Kruss GmbH of Hamburg, Germany. Unless otherwise specified, water contact angles herein are measured using deionized and distilled water on a level sample surface for a sessile drop added from a height of no more than 5 cm in air at 20-25° C. and 20-50% relative humidity. Contact angles reported herein represent averages of 5-9 measured values, discarding both the highest and lowest measured values. The hydrophobicity of the polymer film 410 may be further enhanced with a hydrophobic coating of other materials, such as silicones and fluorocarbons, either as coated from a liquid or plasma coated.

The polymer film 410 may also be suitable for welding to other layers, including the manifold 405. For example, the polymer film 410 may be adapted for welding to polyurethane foams using heat, radio frequency (RF) welding, or other methods to generate heat, such as ultrasonic welding. RF welding may be particularly suitable for more polar materials, such as polyurethane, polyamides, polyesters and acrylates. Sacrificial polar interfaces may be used to facilitate RF welding of less polar film materials, such as polyethylene.

The area density of the polymer film 410 may vary according to a prescribed therapy or application. In some embodiments, an area density of less than 40 grams per square meter may be suitable, and an area density of about 20-30 grams per square meter may be particularly advantageous for some applications.

In some embodiments, for example, the polymer film 410 may comprise or consist essentially of a hydrophobic polymer, such as a polyethylene film. The simple and inert structure of polyethylene can provide a surface that interacts little, if at all, with biological tissues and fluids. Such a surface may encourage the free flow of liquid and low adherence, which can be particularly advantageous for many applications. More polar films suitable for laminating to a polyethylene film include polyamide, co-polyesters, ionomers, and acrylics. To aid in the bond between a polyethylene and polar film, tie layers may be used, such as ethylene vinyl acetate or modified polyurethanes. An ethyl methyl acrylate (EMA) film may also have suitable hydrophobic and welding properties for some configurations.

As illustrated in the example of FIG. 4, the polymer film 410 may have one or more fluid restrictions 420, which can be distributed uniformly or randomly across the polymer film 410. The fluid restrictions 420 may be bi-directional and pressure-responsive. For example, the fluid restrictions 420 can generally comprise or consist essentially of an elastic passage through the polymer film 410 that is normally unstrained to substantially reduce liquid flow, and the elastic passage can expand in response to a pressure gradient. In some embodiments, the fluid restrictions 420 may comprise or consist essentially of perforations in the polymer film 410. Perforations may be formed by removing material from the polymer film 410. For example, perforations may be formed by cutting through the polymer film 410, which may also deform the edges of the perforations in some embodiments. In the absence of a pressure gradient across the perforations, the passages may be sufficiently small to form a seal or flow restriction, which can substantially reduce or prevent liquid flow. Additionally or alternatively, one or more of the fluid restrictions 420 may be an elastomeric valve that is normally closed when unstrained to substantially prevent liquid flow and can open in response to a pressure gradient. A fenestration in the polymer film 410 may be a suitable valve for some applications. Fenestrations may also be formed by removing material from the polymer film 410, but the amount of material removed and the resulting dimensions of the fenestrations may be up to an order of magnitude less than perforations, and may not deform the edges.

For example, some embodiments of the fluid restrictions 420 may comprise or consist essentially of one or more slots or combinations of slots in the polymer film 410. In some examples, the fluid restrictions 420 may comprise or consist of linear slots having a length less than 4 millimeters and a width less than 1 millimeter. The length may be at least 2 millimeters, and the width may be at least 0.4 millimeters in some embodiments. A length of about 3 millimeters and a width of about 0.8 millimeter may be particularly suitable for many applications. A tolerance of about 0.1 millimeter may also be acceptable. Slots of such configurations may function as imperfect valves that substantially reduce liquid flow in a normally closed or resting state. For example, such slots may form a flow restriction without being completely closed or sealed. The slots can expand or open wider in response to a pressure gradient to allow increased liquid flow.

The gel layer 415 may comprise or consist essentially of a fixation layer having a tacky surface and may be formed from a soft polymer suitable for providing a fluid seal with a tissue site. The gel layer 415 may be a polymer gel having a coating weight of about 450 g.s.m., and may have a substantially flat surface in some examples. For example, the gel layer 415 may comprise, without limitation, a silicone gel, hydrocolloid, hydrogel, polyurethane gel, polyolefin gel, hydrogenated styrenic copolymer gel, or a foamed gel. In some embodiments, the gel layer 415 may have a thickness between about 200 microns (μm) and about 1000 microns (μm). In some embodiments, the gel layer 415 may have a hardness between about 5 Shore OO and about 80 Shore OO. Further, the gel layer 415 may be comprised of hydrophobic or hydrophilic materials.

The gel layer 415 may have a periphery 425 surrounding or around an interior portion 430, and apertures 435 disposed through the periphery 425 and the interior portion 430. The interior portion 430 may correspond to a surface area of the manifold 405 in some examples. The gel layer 415 may also have corners 440 and edges 445. The corners 440 and the edges 445 may be part of the periphery 425. The gel layer 415 may have an interior border 450 around the interior portion 430, disposed between the interior portion 430 and the periphery 425. The interior border 450 may be substantially free of the apertures 435, as illustrated in the example of FIG. 4. In some examples, as illustrated in FIG. 4, the interior portion 430 may be symmetrical and centrally disposed in the gel layer 415.

The apertures 435 may have a uniform distribution pattern or may be randomly distributed in the gel layer 415. The apertures 435 in the gel layer 415 may have many shapes, including circles, squares, stars, ovals, polygons, slits, complex curves, rectilinear shapes, triangles, for example, or may have some combination of such shapes.

Each of the apertures 435 may have uniform or similar geometric properties. For example, in some embodiments, each of the apertures 435 may be circular apertures, having substantially the same diameter. In some embodiments, the diameter of each of the apertures 435 may be between about 1 millimeter and about 50 millimeters. In other embodiments, the diameter of each of the apertures 435 may be between about 1 millimeter and about 20 millimeters.

In other embodiments, geometric properties of the apertures 435 may vary. For example, the diameter of the apertures 435 may vary depending on the position of the apertures 435 in the gel layer 415, as illustrated in FIG. 4. In some embodiments, the diameter of the apertures 435 in the periphery 425 of the gel layer 415 may be larger than the diameter of the apertures 435 in the interior portion 430 of the gel layer 415. For example, in some embodiments, the apertures 435 disposed in the periphery 425 may have a diameter between about 9.8 millimeters and about 10.2 millimeters. In some embodiments, the apertures 435 disposed in the corners 440 may have a diameter between about 7.75 millimeters and about 8.75 millimeters. In some embodiments, the apertures 435 disposed in the interior portion 430 may have a diameter between about 1.8 millimeters and about 2.2 millimeters. In other embodiments, the apertures 435 disposed in the interior portion 430 may be slots having a width of about 2 millimeters and a length of about 3 millimeters.

At least one of the apertures 435 in the periphery 425 of the gel layer 415 may be positioned at the edges 445 of the periphery 425 and may have an interior cut open or exposed at the edges 445 that is in fluid communication in a lateral direction with the edges 445. The lateral direction may refer to a direction toward the edges 445 and in the same plane as the gel layer 415. As shown in the example of FIG. 4, the apertures 435 in the periphery 425 may be positioned proximate to or at the edges 445 and in fluid communication in a lateral direction with the edges 445. The apertures 435 positioned proximate to or at the edges 445 may be spaced substantially equidistant around the periphery 425 as shown in the example of FIG. 4. Alternatively, the spacing of the apertures 435 proximate to or at the edges 445 may be irregular.

In the example of FIG. 4, the dressing 110 may further include an attachment device, such as an adhesive 455. The adhesive 455 may be, for example, a medically-acceptable, pressure-sensitive adhesive that extends about a periphery, a portion, or the entire cover 140. In some embodiments, for example, the adhesive 455 may be an acrylic adhesive having a coating weight between 25-65 grams per square meter (g.s.m.). Thicker adhesives, or combinations of adhesives, may be applied in some embodiments to improve the seal and reduce leaks. The adhesive 455 may be a layer having substantially the same shape as the periphery 425. In some embodiments, such a layer of the adhesive 455 may be continuous or discontinuous. Discontinuities in the adhesive 455 may be provided by apertures or holes (not shown) in the adhesive 455. The apertures or holes in the adhesive 455 may be formed after application of the adhesive 455 or by coating the adhesive 455 in patterns on a carrier layer, such as, for example, a side of the cover 140. Apertures or holes in the adhesive 455 may also be sized to enhance the moisture-vapor transfer rate of the dressing 110 in some example embodiments.

As illustrated in the example of FIG. 4, in some embodiments, a release liner 460 may be attached to or positioned adjacent to the gel layer 415 to protect the adhesive 455 prior to use. The release liner 460 may also provide stiffness to assist with, for example, deployment of the dressing 110. Examples of the release liner 460 may include a casting paper, a film, or polyethylene. Further, in some embodiments, the release liner 460 may be a polyester material such as polyethylene terephthalate (PET), or similar polar semi-crystalline polymer. The use of a polar semi-crystalline polymer for the release liner 460 may substantially preclude wrinkling or other deformation of the dressing 110. For example, the polar semi-crystalline polymer may be highly orientated and resistant to softening, swelling, or other deformation that may occur when brought into contact with components of the dressing 110 or when subjected to temperature or environmental variations, or sterilization. In some embodiments, the release liner 460 may have a surface texture that may be imprinted on an adjacent layer, such as the gel layer 415. Further, a release agent may be disposed on a side of the release liner 460 that is configured to contact the gel layer 415. For example, the release agent may be a silicone coating and may have a release factor suitable to facilitate removal of the release liner 460 by hand and without damaging or deforming the dressing 110. In some embodiments, the release agent may be a fluorocarbon or a fluorosilicone, for example. In other embodiments, the release liner 460 may be uncoated or otherwise used without a release agent.

FIG. 4 also illustrates one example of a fluid conductor 465 and a dressing interface 470. As shown in the example of FIG. 4, the fluid conductor 465 may be a flexible tube, which can be fluidly coupled on one end to the dressing interface 470. The dressing interface 470 may be an elbow connector, as shown in the example of FIG. 4, which can be placed over an aperture 475 in the cover 140 to provide a fluid path between the fluid conductor 465 and the tissue interface 135.

Figure 5:
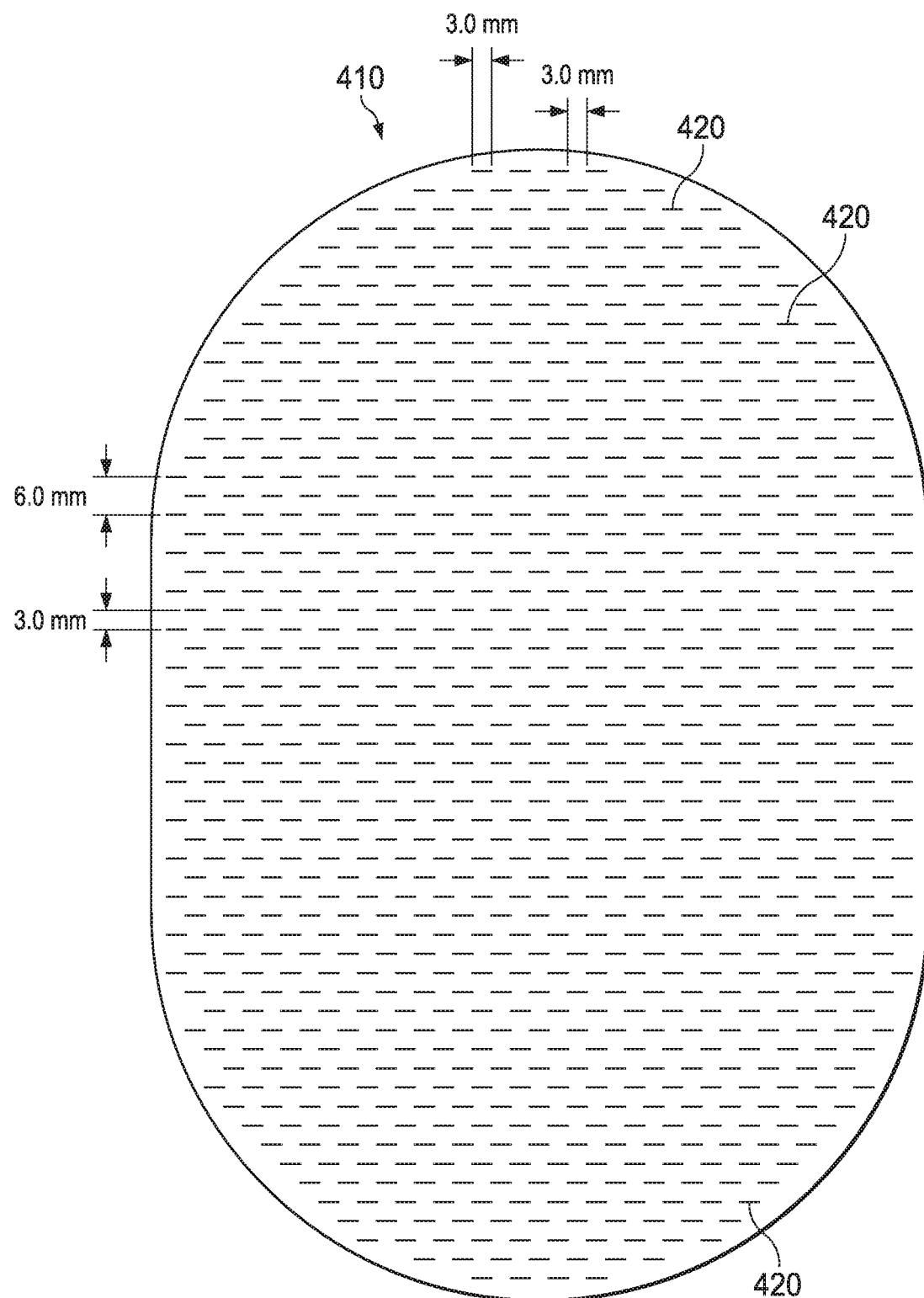
FIG. 5 is a schematic view of an example of a polymer film illustrating additional details that may be associated with some embodiments of the dressing of FIG. 4.

FIG. 5 is a schematic view of an example of the polymer film 410, illustrating additional details that may be associated with some embodiments. As illustrated in the example of FIG. 5, the fluid restrictions 420 may each consist essentially of one or more linear slots having a length of about 3 millimeters. FIG. 5 additionally illustrates an example of a uniform distribution pattern of the fluid restrictions 420. In FIG. 5, the fluid restrictions 420 are substantially coextensive with the polymer film 410 and are distributed across the polymer film 410 in a grid of parallel rows and columns, in which the slots are also mutually parallel to each other. In some embodiments, the rows may be spaced about 3 millimeters on center, and the fluid restrictions 420 within each of the rows may be spaced about 3 millimeters on center, as illustrated in the example of FIG. 5. The fluid restrictions 420 in adjacent rows may be aligned or offset. For example, adjacent rows may be offset, as illustrated in FIG. 5, so that the fluid restrictions 420 are aligned in alternating rows and separated by about 6 millimeters. The spacing of the fluid restrictions 420 may vary in some embodiments to increase the density of the fluid restrictions 420 according to therapeutic requirements.

Figure 6:
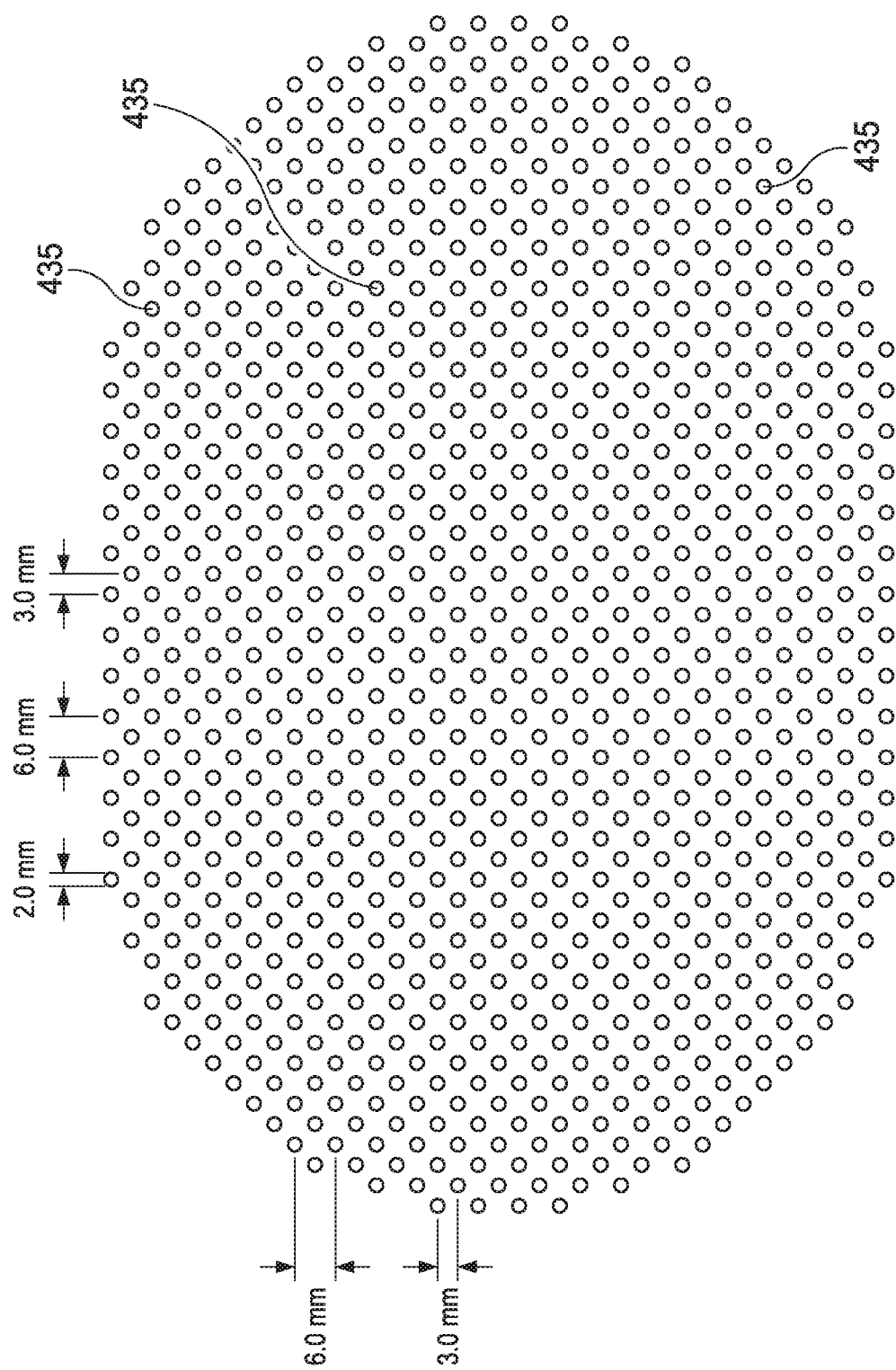
FIG. 6 is a schematic view of an example configuration of apertures that may be associated with some embodiments of the dressing of FIG. 4.

FIG. 6 is a schematic view of an example configuration of the apertures 435, illustrating additional details that may be associated with some embodiments of the gel layer 415. In some embodiments, the apertures 435 illustrated in FIG. 6 may be associated only with the interior portion 430. In the example of FIG. 6, the apertures 435 are generally circular and have a diameter of about 2 millimeters. FIG. 6 also illustrates an example of a uniform distribution pattern of the apertures 435. In FIG. 6, the apertures 435 are distributed in a grid of parallel rows and columns. Within each row and column, the apertures 435 may be equidistant from each other, as illustrated in the example of FIG. 6. FIG. 6 illustrates one example configuration of the apertures 435 that may be particularly suitable for many applications, in which the apertures 435 are spaced about 6 millimeters apart along each row and column, with a 3 millimeter offset.

Figure 7:
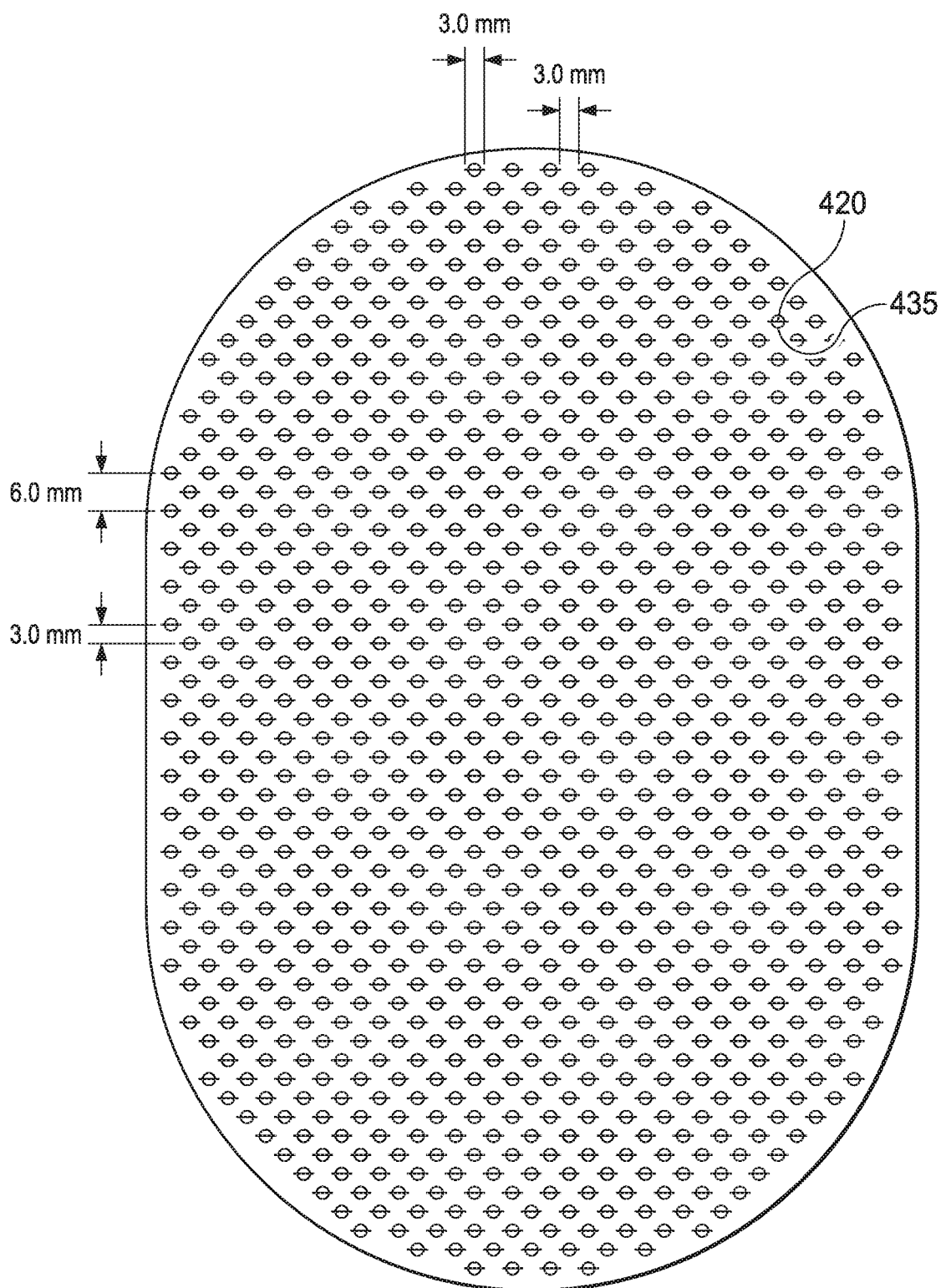
FIG. 7 is a schematic view of an example of a layer having the configuration of apertures of FIG. 6 overlaid on the polymer film of FIG. 5.

FIG. 7 is a schematic view of an example of the gel layer 415 having the configuration of apertures 435 of FIG. 6 overlaid on the polymer film 410 of FIG. 5, illustrating additional details that may be associated with some example embodiments of the tissue interface 135. For example, as illustrated in FIG. 7, the fluid restrictions 420 may be aligned, overlapping, in registration with, or otherwise fluidly coupled to the apertures 435 in some embodiments. In some embodiments, one or more of the fluid restrictions 420 may be registered with the apertures 435 only in the interior portion 430 or only partially registered with the apertures 435. The fluid restrictions 420 in the example of FIG. 7 are generally configured so that each of the fluid restrictions 420 is registered with only one of the apertures 435. In other examples, one or more of the fluid restrictions 420 may be registered with more than one of the apertures 435. For example, any one or more of the fluid restrictions 420 may be a perforation or a fenestration that extends across two or more of the apertures 435. Additionally or alternatively, one or more of the fluid restrictions 420 may not be registered with any of the apertures 435.

As illustrated in the example of FIG. 7, the apertures 435 may be sized to expose a portion of the polymer film 410, the fluid restrictions 420, or both through the gel layer 415. In some embodiments, each of the apertures 435 may be sized to expose no more than two of the fluid restrictions 420. In some examples, the length of each of the fluid restrictions 420 may be substantially equal to or less than the diameter of each of the apertures 435. In some embodiments, the average dimensions of the fluid restrictions 420 are substantially similar to the average dimensions of the apertures 435. For example, the apertures 435 may be elliptical in some embodiments, and the length of each of the fluid restrictions 420 may be substantially equal to the major axis or the minor axis. In some embodiments, though, the dimensions of the fluid restrictions 420 may exceed the dimensions of the apertures 435, and the size of the apertures 435 may limit the effective size of the fluid restrictions 420 exposed to the lower surface of the dressing 110.

Figure 8:
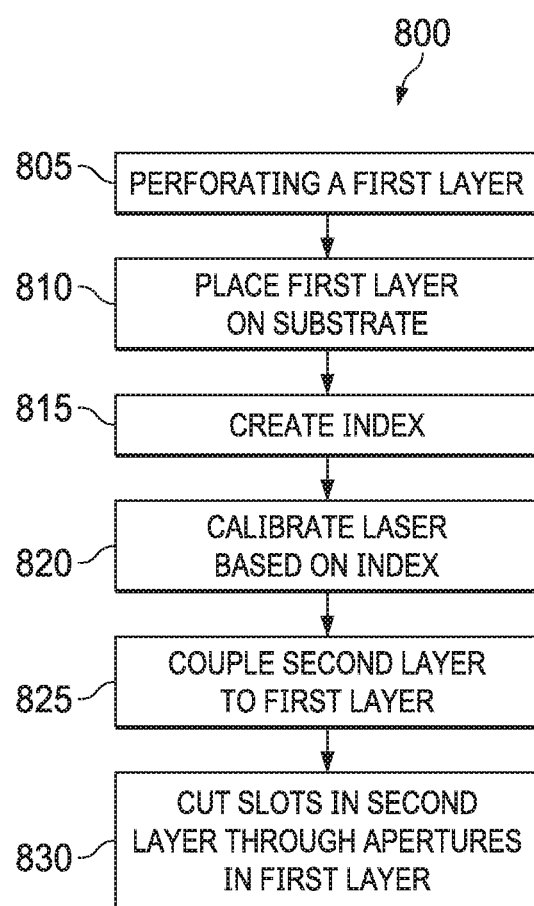
FIG. 8 is a flow diagram illustrating an example method of manufacturing some components of dressings that may be associated with the therapy system of FIG. 1.

FIG. 8 is a flow diagram illustrating an example method 800 of manufacturing some components of the dressing 110. In the example of FIG. 8, a first layer of the dressing 110 can be perforated at 805. For example, the first layer may be the gel layer 415, and the apertures 435 may be formed by a laser or by other suitable techniques for forming the apertures 435 in the gel layer 415. The first layer with perforations can be placed on an assembly substrate at 810. For example, the first layer can be held on a web and then on a roll or liner. An index of the perforations may be created at 815, and the laser or other cutting means may be calibrated at 820 based on the index. A second layer may be coupled to the first layer at 825. The second layer may be the polymer film 410, for example, which may be cut to a preferred size and shape and then loaded and fixed to the gel layer 415. Slots (or slits) may be cut in the second layer through the apertures in the first layer at 830. For example, a combined laminate of the polymer film 410 and the gel layer 415 may be presented to a laser, where the laser calibrates the position of a laser mask to the underside of the combined laminate, referencing the apertures 435 to calibrate its position. The laser can then be fired, creating the fluid restrictions 420 in the polymer film 410, centrally registered within the apertures 435 and having a length substantially equal to or less than the length or diameter of each of the apertures 435. In some embodiments, the fluid restrictions 420 may have a length slightly longer than the length or diameter of the apertures 435 without affecting the performance of the dressing 110.

One or more of the components of the dressing 110 may additionally be treated with an antimicrobial agent in some embodiments. For example, the manifold 405 may be a foam, mesh, or non-woven coated with an antimicrobial agent. In some embodiments, the manifold 405 may comprise antimicrobial elements, such as fibers coated with an antimicrobial agent. Additionally or alternatively, some embodiments of the polymer film 410 may be a polymer coated or mixed with an antimicrobial agent. In other examples, the fluid conductor 465 may additionally or alternatively be treated with one or more antimicrobial agents. Suitable antimicrobial agents may include, for example, metallic silver, PHMB, iodine or its complexes and mixes such as povidone iodine, copper metal compounds, chlorhexidine, or some combination of these materials.

Individual components of the dressing 110 may be bonded or otherwise secured to one another with a solvent or non-solvent adhesive or with thermal welding, for example, without adversely affecting fluid management. Further, the manifold 405 or the polymer film 410 may be coupled to the border 450 of the gel layer 415 in any suitable manner, such as with a weld or an adhesive, for example.

The manifold 405, the polymer film 410, the gel layer 415, the cover 140, or various combinations may be assembled before application or in situ. For example, the cover 140 may be laminated to the manifold 405, and the polymer film 410 may be laminated to the manifold 405 opposite the cover 140 in some embodiments. The gel layer 415 may also be coupled to the polymer film 410 opposite the manifold 405 in some embodiments. In some embodiments, one or more layers of the tissue interface 135 may coextensive. For example, the manifold 405 may be coextensive with the polymer film 410, as illustrated in the embodiment of FIG. 4. In some embodiments, the dressing 110 may be provided as a single, composite dressing. For example, the gel layer 415 may be coupled to the cover 140 to enclose the manifold 405 and the polymer film 410, wherein the gel layer 415 is configured to face a tissue site.

In use, the release liner 460 (if included) may be removed to expose the gel layer 415, which may be placed within, over, on, or otherwise proximate to a tissue site, particularly a surface tissue site and adjacent epidermis. The gel layer 415 and the polymer film 410 may be interposed between the manifold 405 and a tissue site, which can substantially reduce or eliminate adverse interaction with the manifold 405. For example, the gel layer 415 may be placed over a surface wound (including edges of the wound) and undamaged epidermis to prevent direct contact with the manifold 405. Treatment of a surface wound, or placement of the dressing 110 on a surface wound, includes placing the dressing 110 immediately adjacent to the surface of the body or extending over at least a portion of the surface of the body. Treatment of a surface wound does not include placing the dressing 110 wholly within the body or wholly under the surface of the body, such as placing a dressing within an abdominal cavity. In some applications, the interior portion 430 of the gel layer 415 may be positioned adjacent to, proximate to, or covering a tissue site. In some applications, at least some portion of the polymer film 410, the fluid restrictions 420, or both may be exposed to a tissue site through the gel layer 415. The periphery 425 of the gel layer 415 may be positioned adjacent to or proximate to tissue around or surrounding the tissue site. The gel layer 415 may be sufficiently tacky to hold the dressing 110 in position, while also allowing the dressing 110 to be removed or re-positioned without trauma to a tissue site.

Removing the release liner 460 can also expose the adhesive 455, and the cover 140 may be attached to an attachment surface. For example, the cover 140 may be attached to epidermis peripheral to a tissue site, around the manifold 405 and the polymer film 410. The adhesive 455 may be in fluid communication with an attachment surface through the apertures 435 in at least the periphery 425 of the gel layer 415 in some embodiments. The adhesive 455 may also be in fluid communication with the edges 445 through the apertures 435 exposed at the edges 445.

Once the dressing 110 is in a desired position, the adhesive 455 may be pressed through the apertures 435 to bond the dressing 110 to the attachment surface. The apertures 435 at the edges 445 may permit the adhesive 455 to flow around the edges 445 for enhancing the adhesion of the edges 445 to an attachment surface.

In some embodiments, apertures or holes in the gel layer 415 may be sized to control the amount of the adhesive 455 in fluid communication with the apertures 435. For a given geometry of the corners 440, the relative sizes of the apertures 435 may be configured to maximize the surface area of the adhesive 455 exposed and in fluid communication through the apertures 435 at the corners 440. For example, as shown in FIG. 4, the edges 445 may intersect at substantially a right angle, or about 90 degrees, to define the corners 440. In some embodiments, the corners 440 may have a radius of about 10 millimeters. Further, in some embodiments, three of the apertures 435 having a diameter between about 7.75 millimeters to about 8.75 millimeters may be positioned in a triangular configuration at the corners 440 to maximize the exposed surface area for the adhesive 455. In other embodiments, the size and number of the apertures 435 in the corners 440 may be adjusted as necessary, depending on the chosen geometry of the corners 440, to maximize the exposed surface area of the adhesive 455. Further, the apertures 435 at the corners 440 may be fully contained within the gel layer 415, substantially precluding fluid communication in a lateral direction exterior to the corners 440. The apertures 435 at the corners 440 being fully housed within the gel layer 415 may substantially preclude fluid communication of the adhesive 455 exterior to the corners 440 and may provide improved handling of the dressing 110 during deployment at a tissue site. Further, the exterior of the corners 440 being substantially free of the adhesive 455 may increase the flexibility of the corners 440 to enhance comfort.

In some embodiments, the bond strength of the adhesive 455 may vary in different locations of the dressing 110. For example, the adhesive 455 may have lower bond strength in locations adjacent to the gel layer 415 where the apertures 435 are relatively larger and may have higher bond strength where the apertures 435 are smaller. Adhesive 455 with lower bond strength in combination with larger apertures 435 may provide a bond comparable to adhesive 455 with higher bond strength in locations having smaller apertures 435.

The geometry and dimensions of the tissue interface 135, the cover 140, or both may vary to suit a particular application or anatomy. For example, the geometry or dimensions of the tissue interface 135 and the cover 140 may be adapted to provide an effective and reliable seal against challenging anatomical surfaces, such as an elbow or heel, at and around a tissue site. Additionally or alternatively, the dimensions may be modified to increase the surface area for the gel layer 415 to enhance the movement and proliferation of epithelial cells at a tissue site and reduce the likelihood of granulation tissue in-growth.

Further, the dressing 110 may permit re-application or re-positioning to reduce or eliminate leaks, which can be caused by creases and other discontinuities in the dressing 110 and a tissue site. The ability to rectify leaks may increase the reliability of the therapy and reduce power consumption in some embodiments.

If not already configured, the dressing interface 470 may disposed over the aperture 475 and attached to the cover 140. The fluid conductor 465 may be fluidly coupled to the dressing interface 470 and to the negative-pressure source 105.

In operation, the dressing 110 can provide a sealed therapeutic environment proximate to a tissue site, substantially isolated from the external environment, and the negative-pressure source 105 can reduce pressure in the sealed therapeutic environment.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudate and other fluid flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source, and this descriptive convention should not be construed as a limiting convention.

Negative pressure applied across the tissue site through the tissue interface 135 in the sealed therapeutic environment can induce macro-strain and micro-strain in the tissue site. Negative pressure can also remove exudate and other fluid from a tissue site, which can be collected in container 115.

Negative pressure applied through the tissue interface 135 can create a negative pressure differential across the fluid restrictions 420 in the polymer film 410, which can open or expand the fluid restrictions 420 from their resting state. For example, in some embodiments in which the fluid restrictions 420 may comprise substantially closed fenestrations through the polymer film 410, a pressure gradient across the fenestrations can strain the adjacent material of the polymer film 410 and increase the dimensions of the fenestrations to allow liquid movement through them, similar to the operation of a duckbill valve. Opening the fluid restrictions 420 can allow exudate and other liquid movement through the fluid restrictions 420 into the manifold 405 and the container 115. Changes in pressure can also cause the manifold 405 to expand and contract, and the interior border 450 may protect the epidermis from irritation. The polymer film 410 and the gel layer 415 can also substantially reduce or prevent exposure of tissue to the manifold 405, which can inhibit growth of tissue into the manifold 405.

In some embodiments, the manifold 405 may be hydrophobic to minimize retention or storage of liquid in the dressing 110. In other embodiments, the manifold 405 may be hydrophilic. In an example in which the manifold 405 may be hydrophilic, the manifold 405 may also wick fluid away from a tissue site, while continuing to distribute negative pressure to the tissue site. The wicking properties of the manifold 405 may draw fluid away from a tissue site by capillary flow or other wicking mechanisms, for example. An example of a hydrophilic material suitable for some embodiments of the manifold 405 is a polyvinyl alcohol, open-cell foam such as V.A.C. WHITEFOAM™ dressing available from KCI of San Antonio, Tex. Other hydrophilic foams may include those made from polyether. Other foams that may exhibit hydrophilic characteristics include hydrophobic foams that have been treated or coated to provide hydrophilicity.

If the negative-pressure source 105 is removed or turned-off, the pressure differential across the fluid restrictions 420 can dissipate, allowing the fluid restrictions 420 to move to their resting state and prevent or reduce the rate at which exudate or other liquid from returning to the tissue site through the polymer film 410.

In some applications, a filler may also be disposed between a tissue site and the gel layer 415. For example, if the tissue site is a surface wound, a wound filler may be applied interior to the periwound, and the gel layer 415 may be disposed over the periwound and the wound filler. In some embodiments, the filler may be a manifold, such as open-cell foam. The filler may comprise or consist essentially of the same material as the manifold 405 in some embodiments.

Additionally or alternatively, instillation solution or other fluid may be distributed to the dressing 110, which can increase the pressure in the tissue interface 135. The increased pressure in the tissue interface 135 can create a positive pressure differential across the fluid restrictions 420 in the polymer film 410, which can open or expand the fluid restrictions 420 from their resting state to allow the instillation solution or other fluid to be distributed to a tissue site.

In some embodiments, the controller 120 may receive and process data from one or more sensors, such as the first sensor 125. The controller 120 may also control the operation of one or more components of the therapy system 100 to manage the pressure delivered to the tissue interface 135. In some embodiments, controller 120 may include an input for receiving a desired target pressure and may be programmed for processing data relating to the setting and inputting of the target pressure to be applied to the tissue interface 135. In some example embodiments, the target pressure may be a fixed pressure value set by an operator as the target negative pressure desired for therapy at a tissue site and then provided as input to the controller 120. The target pressure may vary from tissue site to tissue site based on the type of tissue forming a tissue site, the type of injury or wound (if any), the medical condition of the patient, and the preference of the attending physician. After selecting a desired target pressure, the controller 120 can operate the negative-pressure source 105 in one or more control modes based on the target pressure and may receive feedback from one or more sensors to maintain the target pressure at the tissue interface 135.

The systems, apparatuses, and methods described herein may provide significant advantages over prior art. For example, some dressings for negative-pressure therapy can require time and skill to be properly sized and applied to achieve a good fit and seal. In contrast, some embodiments of the dressing 110 can provide a negative-pressure dressing that is simple to apply, reducing the time to apply and remove. In some embodiments, for example, the dressing 110 may be a fully-integrated negative-pressure therapy dressing that can be applied to a tissue site (including on the periwound) in one step, without being cut to size, while still providing or improving many benefits of other negative-pressure therapy dressings that require sizing. Such benefits may include good manifolding, beneficial granulation, protection of the peripheral tissue from maceration, and a low-trauma and high-seal bond. These characteristics may be particularly advantageous for surface wounds having moderate depth and medium-to-high levels of exudate. The dressing 110 can also be manufactured with automated processes with high throughput, which can lower part costs. Some embodiments of the dressing 110 may remain on a tissue site for at least 5 days, and some embodiments may remain for at least 7 days. Antimicrobial agents in the dressing 110 may extend the usable life of the dressing 110 by reducing or eliminating infection risks that may be associated with extended use, particularly use with infected or highly exuding wounds.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 110, the container 115, or both may be eliminated or separated from other components for manufacture or sale. In other example configurations, the controller 120 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A method of manufacturing a dressing for negative-pressure treatment, the method comprising:
    perforating a first layer to create a plurality of apertures in the first layer;
    creating an index of the plurality of apertures in the first layer;
    placing a second layer adjacent to the first layer; and
    cutting a plurality of slots in the second layer, wherein each of the slots is cut through one of the apertures in the first layer based on the index.

2. The method of claim 1, wherein each of the slots is centered in one of the apertures.

3. The method of claim 1, wherein the first layer is a gel layer.

4. The method of claim 1, wherein:
the first layer is a gel layer; and
the second layer is a polymer film.

5. The method of claim 1, wherein:
each of the slots has a length not greater than a length or diameter of each of the apertures; and
each of the slots has a width not greater than a width or diameter of each of the apertures.

6. The method of claim 1, further comprising:
bonding the second layer to a manifold; and
bonding a cover to the first layer around the second layer and the manifold.

* * * * *